United States Patent
Bunn et al.

[19]

[11] Patent Number: 6,096,562
[45] Date of Patent: Aug. 1, 2000

[54] MULTI-SLIDE ASSEMBLY INCLUDING SLIDE, FRAME AND STRIP CAP, AND METHODS THEREOF

[75] Inventors: Kenneth E. Bunn, Warrenton, Va.; Abdul Wahid Khan, Naperville, Ill.; Susan K. W. Nanda, Naperville, Ill.; Barbara Myszkiewicz Sullivan, Naperville, Ill.; Keith O. Whittlinger, Batavia, Ill.; Kathleen R. Williamson, Wheeling, Ill.; Hoyt E. Matthai, Middletown, Md.

[73] Assignee: Nalge Nunc International Corporation, Rochester, N.Y.

[21] Appl. No.: 08/958,521

[22] Filed: Oct. 27, 1997

[51] Int. Cl.⁷ .................................................. G01N 33/543
[52] U.S. Cl. ............................. 436/518; 422/58; 422/99; 422/102; 435/287.1; 435/287.2; 435/288.3; 435/288.4; 435/283.1; 436/527; 436/531; 436/809
[58] Field of Search .............................. 422/58, 99, 102; 435/283.1, 287.1, 287.2, 288.3, 288.4; 436/518, 527, 531, 809

[56] References Cited

U.S. PATENT DOCUMENTS

| Re. 34,841 | 1/1995 | Suovaniemi et al. | 356/244 |
|---|---|---|---|
| 3,649,464 | 3/1972 | Freeman | 195/140 |
| 3,726,767 | 4/1973 | White | 195/127 |
| 3,745,091 | 7/1973 | McCormick | 195/139 |
| 3,746,161 | 7/1973 | Jones | 206/72 |
| 3,907,505 | 9/1975 | Beall et al. | 23/259 |
| 3,961,346 | 6/1976 | White | 356/244 |
| 4,659,222 | 4/1987 | Ekholm | 356/244 |
| 4,715,911 | 12/1987 | Johansson et al. | 156/69 |
| 4,877,659 | 10/1989 | Vince | 428/34.1 |
| 4,891,321 | 1/1990 | Hubscher | 435/293 |
| 5,084,246 | 1/1992 | Lyman et al. | 422/101 |
| 5,110,556 | 5/1992 | Lyman et al. | 422/101 |
| 5,141,718 | 8/1992 | Clark | 422/99 |
| 5,308,584 | 5/1994 | Vauramo | 422/104 |
| 5,358,692 | 10/1994 | Reynolds | 422/104 |
| 5,514,343 | 5/1996 | Verwohlt et al. | 422/104 |

OTHER PUBLICATIONS

Slide Flask Product Literature, Nunc A/S (1988).
Lab–Tek® Product Literature, Nange Nunc International (no date).
Lab–Tek® II Chamber Slide System Product Literature, Nalge Nunc International (no date).
Lab–Tek® II Chambered Coverglass Product Literature, Nalge Nun International (no date).
Amplification Workstation Product Literature, Nalge Nunc International (no date).
Nunc SlideFlask Procedures, Nunc A/S (1986).
Welding Parameters disclosed at page 12 of U.S. Patent Application Serial No. 08/958,521.
NUNC™ Products 1996 Catalog, Nalge Nunc International (1996), in particular, pp. 19, 38.
SonicSeal Slide ™ Well Product Literature, Nalge Nunc International (no date).

*Primary Examiner*—Christopher L. Chin
*Attorney, Agent, or Firm*—Wood, Herron & Evans, L.L.P.

[57] ABSTRACT

A multi-slide assembly includes various components that alone or in combination facilitate testing of test samples with minimal manipulation of assay components. Moreover, the various device components permit centrifugation, culturing and analysis of each test sample to be performed in the same assembly. A frame retains a plurality of reaction vessel assemblies between a pair of opposing channels that are configured to slidably receive the opposing ends of each reaction vessel assembly. A strip cap seals the openings in each reaction vessel using cap members having sealing rings circumscribing the external walls thereof to form compression seals with internal walls of the reaction vessels. Furthermore, in a method of making a multi-well slide assembly, an ultrasonic welding process removably bonds a plurality of wells to a slide plate to provide an adequate seal therebetween during centrifugation, yet still enable separation thereof by an operator.

49 Claims, 6 Drawing Sheets

MULTI-SLIDE ASSEMBLY INCLUDING SLIDE, FRAME AND STRIP CAP, AND METHODS THEREOF

FIELD OF THE INVENTION

The invention is generally directed to cell culturing, immunological and molecular tools for use in biomedical research and diagnostics applications. More specifically, the invention is directed to cell culture, immunological and molecular tools such as slides, wells, vessels and the like for use in research or diagnostic testing of biological test samples.

BACKGROUND OF THE INVENTION

Cell culture vessels such as flasks, dishes, slides, wells, culture tubes and the like are utilized in a number of biomedical diagnostics applications to test for the presence of microorganisms in test samples such as patient specimens from humans or other animals. Likewise, other types of reaction vessels similar in format but differing in surface characteristics to cell culture vessels are utilized for immunological, molecular and biochemical analysis of the same.

For example, microorganisms may be tested for to assist in the diagnosis of an infection. Some infectious diseases are distinctive enough to be identified clinically. Most pathogens, however, can cause a wide spectrum of clinical symptoms in humans, many of which are not unique to a particular pathogen. Therefore, it is often necessary to use microbiologic laboratory methods to identify the specific organism that is causing a disease.

One method used to detect the presence of a microorganism causing an infection is to isolate and culture in an artificial medium the microorganism causing the infection. Both the presence and number of microorganisms in a patient's specimen can assist in defining the cause of a disease. To use this process, a specimen from a patient is placed in a liquid, solid or semi-solid medium that permits the growth of selective microorganisms. The medium may also include inhibitory substances that prevent the growth of microorganisms in the medium, other than the microorganisms the maker of the medium has selected. If the microorganism is present in the patient's specimen, it will grow in the medium and its growth will be detected.

Another method that may be used to identify the presence of a microorganism is to expose a living cell line that is known to be susceptible to particular microorganisms to a test sample from a patient. If the microorganism is present in the patient's specimen, the cells may exhibit cytopathic effects induced by that microorganism, which may be detected and confirmed by a fluorescent labeled monoclonal antibody. Typically, with such a process a cell line is grown on a suitable surface such as a cover slip disposed in the Petri dish, dram vial, culture tube or other vessel. Alternatively, the cell culture may be grown directly on the surface of a suitable vessel. The cell culture is inoculated with a clinical test sample, and then some of these vessels may be centrifuged to quickly introduce the microorganism into the cells. Typically, the cell culture is then incubated for a period of time to grow the organism, whereby the presence or non-presence of the microorganism is later analyzed, typically through visual inspection using an optical reader such as a microscope.

In many cases, to grow or culture cells both a solid surface and a liquid medium are needed. The solid surface provides a location upon which the cells can adhere, and the solid support typically mimics the cell's natural environment in the tissue from which they were derived. Often, the flat surfaces of tissue-culture flasks, trays, Petri dishes, multi-well culture plates, and even the inside surfaces of large roller bottles make ideal support surfaces for growing cells.

The medium in which the cells are immersed is the cells' source of nutrients. It is an artificial environment similar enough to the cells' natural environment to permit their continued growth and proliferation. The basic formulas of culture media typically consist of water, salts and amino acids, to which supplements such as serum, antibiotics, or growth factors can be added.

Most cell culture vessels are typically not well suited for performing all tasks in a diagnostic process. For example, a culture tube or Petri dish is often suitable for inoculation and/or incubation; however, many such cell culture vessels are not well suited for centrifugation and/or analysis. In general, cell growth occurs best on a modified plastic surface, while analysis and other processing is best performed on a glass surface. Consequently, test samples often must be transported between various vessels during the diagnostic process. Moreover, with vessels such as dram vials, culture tubes or Petri dishes, each test sample must be handled individually, which can become cumbersome when working with numerous samples.

Multi-well culture plates may also be used in diagnostic testing. A multi-well plate has multiple wells formed into a two-dimensional array within which one or more cell lines are grown. Often, however, such multi-well plates are restrictive in that it is difficult to culture multiple cell lines in a single plate due to different culture times required for each type of cell line. Moreover, there is a possibility of cross-contamination between wells. Also, if one cell culture in a multi-well plate becomes contaminated or otherwise inoperative, typically the entire plate must be discarded.

It has also been found that centrifugation causes a number of concerns with many conventional cell culture vessels. Typically, such vessels must be relatively sturdy to withstand the forces that occur in centrifugation. Moreover, an adequate seal must be maintained during centrifugation to prevent loss of the cell culture and/or contamination of other cultures, or the laboratory environment.

Accordingly, it is desirable to maintain a tight seal with various cell culture vessels subjected to centrifugation. However, a tight seal on a vessel may induce an aerosol effect when the sealing member for the vessel is removed. It should be appreciated that whenever a sealing member is removed under a tight seal, a vacuum is temporarily induced in the vessel. When the vacuum is released after the sealing member is fully removed, viruses or other biological agents or contaminants may be released into the atmosphere due to the sudden pressure change in the vessel. Such agents may be dangerous to operators, and they may also cause contamination of nearby samples.

Another concern is the vaporization of certain harmful processing chemicals such methanol, ethanol, isopropanol, dimethyl suphoxide (DMSO), phenol, or chloroform. Consequently, great care must be taken in removing a sealing member from conventional cell culture vessels.

Another conventional cell culture vessel is a multi-well slide assembly such as the SonicSeal four well slide available from Nalge Nunc International, which includes multiple wells joined together and secured to a slide plate through a breakable ultrasonic weld. An opener may be used to remove the upper structure of the wells from the slide plate such that the cell cultures disposed on the slide plate may be analyzed. However, such assemblies are not designed for centrifugation and include no suitable manner of sealing each well during centrifugation. The loose-fitting lid provided with such assemblies is insufficient to tightly seal each well.

Such assemblies are typically welded together using a two-step ultrasonic welding process. The upper structure is provided with a thin flange with a triangular cross-section on a mating end thereof (commonly referred to as an energy director) that is melted during ultrasonic welding to weld the upper structure to the slide plate. In the first step, the upper structure is ultrasonically welded to a distance of approximately one half of the length of the energy director to energize the molecules therein. Then, in the second step, a stronger weld is formed between the upper structure and slide plate through limited additional ultrasonic welding that further energizes the molecules but does not cause the energy director to become completely fused—thereby providing the break-apart property of the slide. After bonding, about 88 percent of the energy director is used up, with the mating surface between the upper structure and slide being only about 0.015 inches wide, which is only about 88 percent of the width of the base of the energy director, and only about 34 percent of the thickness of the sidewalls of the upper structure. The resulting bond is air- and liquid-proof and has sufficiently high mechanical strength for culturing purposes. However, the bond tends to leak during and/or after exposure to centrifugation forces, and thus is not suited for use in a centrifuge.

Therefore, a significant need exists for improved tools and an enhanced manner of performing cell culturing, diagnosis and/or testing of biological test samples with greater efficiency, reliability and accuracy. Specifically, a need exists for tools that are particularly suited for multiple activities to minimize the effort, time and potential contamination concerns associated with transferring test samples, cell cultures and the like between vessels.

SUMMARY OF THE INVENTION

The invention addresses these and other problems associated with the prior art in providing a multi-slide assembly including various components that alone or in combination facilitate testing of biological, chemical or molecular test samples with minimal manipulation of assay components. Specifically, various operations such as centrifugation, inoculation, culturing and/or analysis of a test sample may be performed in the same reaction vessel to speed up testing and/or to minimize cross-contamination between multiple samples. Batch processing of numerous test samples may therefore be performed expediently and reliably.

Consistent with one aspect of the invention, a method is provided for testing a test sample in which a reaction vessel defined at least partially by a sidewall member removably coupled to a slide plate is inoculated with a test sample and centrifuged. In addition, the sidewall member is separated from the slide plate to permit analysis of the test sample on the slide plate.

Consistent with another aspect of the invention, a frame is used to retain a plurality of reaction vessels, with each reaction vessel including opposing ends. The frame includes a pair of opposing channels including first and second ends and configured to slidably receive the opposing ends of each reaction vessel, and first and second retaining mechanisms respectively disposed proximate the first and second ends of the pair of opposing channels and configured to retain each reaction vessel within the pair of opposing channels.

Consistent with yet another aspect of the invention, a method is provided for performing a common operation on a plurality of test samples, each test sample being housed in one of a plurality of reaction vessels, each vessel of the type including opposing ends. The method includes placing the plurality of reaction vessels in a frame including a pair of opposing channels including first and second ends and slidably receiving the opposing ends of each reaction vessel, and first and second retaining mechanisms respectively disposed proximate the first and second ends of the pair of opposing channels and retaining each vessel within the pair of opposing channels. The method also includes performing the common operation on the plurality of test samples while the plurality of reaction vessels are retained in the frame.

Consistent with another aspect of the invention, a strip cap is also provided for use in sealing an opening in the reaction vessel having an internal wall defining the same. The strip cap includes a cap member having an external wall, a mating portion of which is configured to abut the internal wall of the vessel around a perimeter of the opening, and a sealing ring circumscribing the external wall of the cap member and configured to form a compression seal with the internal wall of the vessel.

Consistent with a further aspect of the invention, a multi-well slide is provided including a slide plate, a plurality of wells coupled to the slide plate, each including an internal wall defining an opening to the well, and a strip cap. The strip cap includes a strip member, a plurality of cap members coupled to the strip member, each cap member having an external wall, a mating portion of which is configured to abut the internal wall of one of the plurality of wells around the perimeter of the opening thereto, and a plurality of sealing rings, each sealing ring circumscribing the external wall of one of the plurality of cap members, and each sealing ring configured to form a compression seal with the internal wall of one of the plurality of wells.

Consistent with yet another aspect of the invention, a method of making a reaction vessel of the type including at least one well defined by a sidewall member removably coupled to a slide plate is provided, including forming a bond that is sufficient to withstand centrifugation forces between the sidewall member and the slide plate via ultrasonic welding; and controllably weakening the bond between the sidewall member and the slide plate via ultrasonic welding to permit selective separation of the sidewall member from the slide plate.

Consistent with a further aspect of the invention, a reaction vessel is provided, including a slide plate removably secured to a sidewall member through an ultrasonically-welded and controllably-weakened bond. The sidewall member includes an energy director disposed at an end thereof, the energy director having a base with a width that is substantially equal to that of the sidewall member proximate the end thereof. The bond includes a fused junction between the slide plate and the sidewall member that is formed of substantially the entire energy director and that defines a mating surface that is substantially equal to the width of the base of the energy director.

These and other advantages and features, which characterize the invention, are set forth in the claims annexed hereto and forming a further part hereof. However, for a better understanding of the invention, and of the advantages and objectives attained through its use, reference should be made to the Drawing. and to the accompanying descriptive matter, in which there is described exemplary embodiments of the invention.

BRIEF DESRIPTION OF THE DRAWING

FIG. 1 is an exploded perspective view of a multi-slide assembly consistent with the invention.

FIGS. 2A and 2B respectively illustrate cross-sectional views of an upper structure and slide plate of a multi-well slide before and after ultrasonic welding.

DETAILED DESCRIPTION

Figure 1:
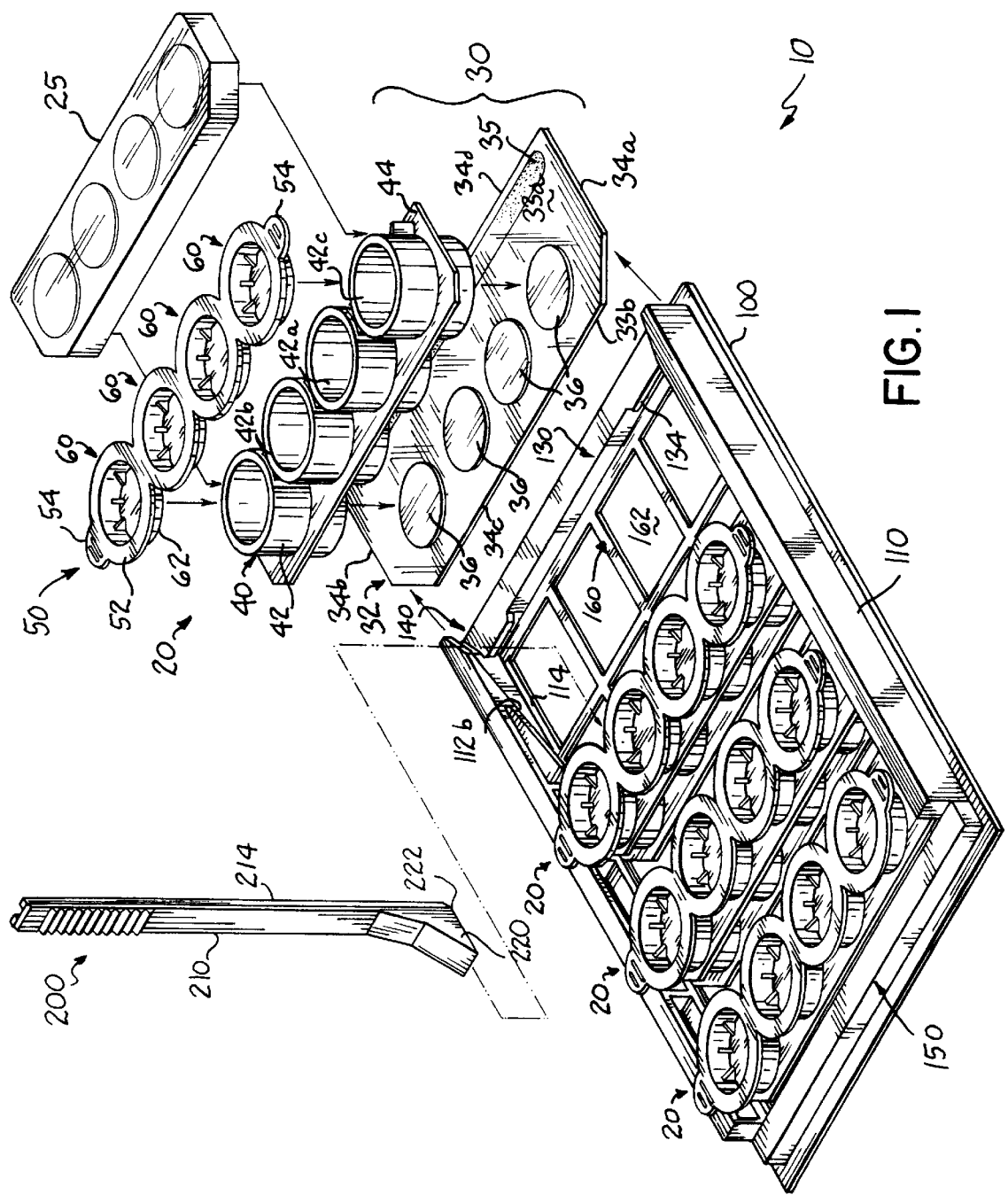

Turning to the Drawing, wherein like numbers denote like parts throughout the several views, FIG. 1 is an exploded perspective view of a multi-slide assembly 10 consistent with the principles of the invention. Assembly 10 generally includes a plurality of multi-well slide assemblies 20, each including a multi-well slide 30 and a strip cap 50. Each assembly 20 may also include a lid 25 that may be used during incubation to cover each multi-well slide when its associated strip cap is removed, thus minimizing potential contamination with microorganisms, dust, etc.

The plurality of multi-well slide assemblies 20 are housed in a frame 100 that is suitable for performing batch operations on the cell cultures within the multi-well slide assemblies. Also shown is a pry-bar opener 200 that may be used to separate the upper structures of the multi-well slides from the slide plates thereof.

The discussion hereinafter will focus on cell culture applications of the invention. However, it should be appreciated that the invention may be utilized in other applications, e.g., in immunological and molecular applications, cell-based assay applications, etc. Consequently, while various components of the embodiments described hereinafter, such as vessels, assemblies, surfaces, and the like, may be described with reference to cell culturing applications, one skilled in the art will appreciate that the principles of the invention may be applied to other applications of reaction vessels and reaction vessel assemblies in general without departing from the spirit and scope of the invention.

Multi-Well Slide Assemblies

Each multi-well slide 30 shown in FIG. 1 includes a slide plate 32 having opposing top and bottom surfaces 33a, 33b, opposing ends 34a, 34b, a beveled front edge 34c and a rear edge 34d. Each slide plate 32 also includes a frosted writing surface 35 and a raised well floor 36 disposed within each well and upon which a cell culture is grown.

An upper structure 40 including a plurality of wells 42 is ultrasonically welded to slide plate 32. Each well 42 forms a cell culture chamber with slide plate 32, and each includes an inner wall 42a and a top edge 42b defining an opening 42c in each well. The plurality of wells 42 are integrally molded to one another and supported by flange 44. Upper structure 40 forms a sidewall member that defines each well in conjunction with slide plate 32. It should be appreciated that other sidewall member designs, e.g., defining any number of wells, may be used in the alternative. For example, a sidewall member may only define one well.

The design of multi-well slide 30 is similar in some respects to the No. 138121 SonicSeal slides available from Nalge Nunc International. The slide plate has standard dimensions of a microscope slide. Moreover, either or both of the slide plate and the upper structure may be formed of Permanox® plastic or other similar materials that have suitable chemical resistance for performing culturing, analysis and other processing, as well as biological compatibility for facilitating cell growth thereon. The upper structure 40 is ultrasonically welded to the slide plate 32 to form a liquid tight seal. Moreover, the upper structure 40 is removable by prying the upper structure from the slide plate 32 with a pry-bar opener 200 that breaks the ultrasonic weld.

The aforementioned SonicSeal slides have been found to not be particularly well-suited to centrifugation due to the lack of strength in the ultrasonic welds used thereon. To address this concern, it is desirable to provide a coupling between the upper structure 40 and slide plate 32 that is suitable of withstanding centrifugation, but which still enables the removal of the upper structure by a user.

Ultrasonic welding in general is known in the art. See, e.g., U.S. Pat. No. 4,715,911, which is incorporated by reference herein. Consistent with the invention, it is desirable to utilize a two-step, weld-by-distance ultrasonic welding process that creates an initial bond in a first welding step that is sufficiently leak-proof during and after centrifugation. Then, in a second welding step, the upper structure and slide plate are further compressed to cause a secondary melt that controllably weakens the bond without compromising the leak-proof seal established by the first step.

Figure 2A:
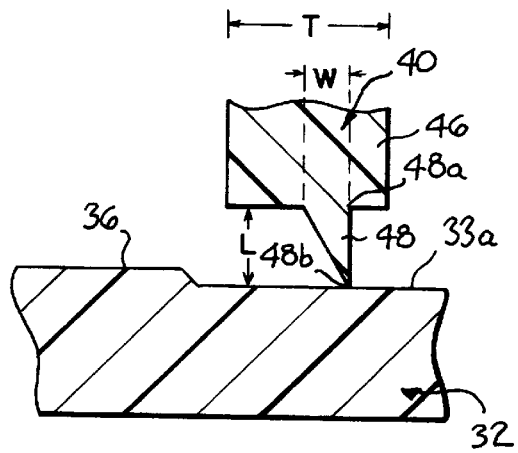

For example, as shown in FIG. 2A, a tapered energy director 48 (e.g., with a triangular cross-section) may be provided on the end of a sidewall 46 on. upper structure 40. Energy director 48 may have a length L of about 0.014 to about 0.024 inches (0.36 to 0.61 mm), more preferably about 0.019 inches (0.49 mm). Energy director 48 tapers at about a 30 degree angle from a base 48a to a tip 48b, with a width W that is preferably about 0.017 inches (0.42 mm). Sidewall 46 to which energy director 48 is coupled preferably has a thickness of about 0.043 inches (1.09 mm).

For the first weld cycle, a pressure of about 15 to about 30 psi, more preferably about 20 psi may be used, with a weld distance of about 0.014 to about 0.019 inches (0.36 to 0.48 mm), more preferably about 0.017 inches (0.42 mm), and a weld duration of about 0.5 to 1.0 seconds, more preferably about 0.8 seconds. The first weld cycle fully bonds the upper structure to the slide plate as a result of the energy director becoming fully molten during welding.

For the second weld cycle, a pressure of about 20 to about 40 psi, more preferably about 30 psi may be used, with a weld distance of about 0.001 to about 0.005 inches (0.03 to 0.13 mm), more preferably about 0.004 inches (0.09 mm), and a weld duration of about 0.5 to 1.0 seconds, more preferably about 0.8 seconds. A dwell time of about 3 to about 10 seconds may be used, more preferably about 5.0 seconds, to permit some cooling of the components while under pressure and thereby minimize failures. Additional suitable weld parameters include a stroke position of about 0.1 inches (2.54 mm), a mechanical stop of about 4.3 inches (109.22 mm), an end weld of about 6.0 inches (152.4 mm), a pre-trigger of about 5.5, a moderate down speed, and a trigger of about 2.0. It should be appreciated that the parameters may vary depending upon the particular ultrasonic welding machine used.

Figure 2B:
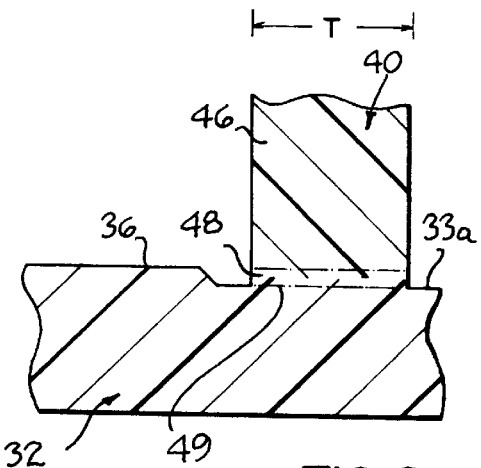

It has been found that, by generating a full weld to approximately the full length of the energy director in a first welding step, a bond is generated between the upper structure and slide plate that can withstand centrifugation forces (e.g. at least 700 G's for an hour) and still be leak-proof during and after centrifugation. Then, by welding in the second weld at least the remaining length of the energy director at a greater pressure (typically about 10 psi greater) than in the first weld, a controlled weakening of the bond may be generated to reduce the breakage resistance of the bond to a level that permits separation of the upper structure from the slide plate, but that is still capable of withstanding centrifugation. In addition, the width of the bond is permitted to occupy, in the minimum, the full width of the energy director, and in the maximum, the full thickness of the sidewall, which is believed to contribute to the improved robustness of the bond compared to conventional designs. In the embodiment discussed above, the total weld distance can be about 0.02 inches (0.51 mm) for a energy director with a length of about 0.019 inches (0.49 mm), and the width of the bond therefore can range from about 0.017 inches (0.42 mm) wide to about 0.043 inches (1.09 mm). Therefore, as shown in FIG. 2B, the resulting bond between slide plate 32 and upper structure 40 uses up the entire energy director, and defines a mating surface 49 therebetween that is substantially the thickness T of sidewall 48.

In addition, it has been found to be beneficial to cool molded components prior to ultrasonic welding. For example, the components may be allowed to air cool for 12–24 hours before welding. Alternatively, a similar degree of cooling may be performed for two or three minutes on an air conditioned cooling conveyor that transports components from the molding process to the welding process.

Conventional welding processes that attempt to first energize the components, and second weld the components together have been found to not provide the same combination of resistance to centrifugation forces and separability with controllable results. For example, a conventional welding process may utilize a two-step process, with a first step utilizing an air pressure of 10 psi, a distance of (0.010 inches, and a weld time of 1.2 seconds, and a second step utilizing an air pressure of 15 psi, a distance of 0.007 inches, and a weld time of 0.5 seconds. Other weld parameters of the conventional process utilize a dwell time of 5.0 seconds, a mechanical stop of 0.420 inches, and end weld of 6.110 inches, a pretrigger of 5.726 inches a trigger of 1.6 and a moderate down speed. Even by increasing welding pressure, time and/or distance to theoretically increase the bond strength, it has been found that conventional processes of this type do not provide suitably consistent results. In particular, it is believed that the width of the bond, which is only a portion of the width of the energy director, and less of a portion of the width of the sidewall, does not provide suitable robustness for centrifugation applications.

In other conventional welding processes, the full length of an energy director may be used up during welding, resulting in a bond that occupies the full width of the sidewalls. However, the bonds resulting from these conventional processes are permanent and are not breakable by an operator without damage to the welded components. Consequently, these processes are not suitable for many of the applications disclosed herein that utilize the separability of a slide plate and an upper structure to perform analysis of test samples.

It should be appreciated that the above-described welding parameters may be varied in different applications. It should be appreciated that materials other than Permanox® plastic may require different welding characteristics. For example, for polystyrene, it may be desirable to utilize a longer energy director (e.g., about 0.025 to about 0.035 inches, or 0.64 to 0.89 mm), with a correspondingly greater weld distance in the first weld step (e.g., about 0.022 to about 0.031 inches, or 0.56 to 0.79 mm).

It should also be appreciated, however, that the design of multi-well slide 30 is but merely one type of cell culture vessel suitable for use with the various components of the invention. For example, various enclosed cell culture vessels including flasks, dishes, culture tubes and structures including a plurality of wells in various geometric shapes, etc. may be used. Moreover, various non-enclosed cell culture vessels such as slides, wafers, discs, plates, microarrayed surfaces, etc. may also be used, as may other types of reaction vessels suitable for other immunological and molecular applications, for example. Accordingly, the invention should not be limited to the particular design of multi-well slide 30, nor specifically to the material and/or the manner of coupling the upper structure to the slide plate, disclosed herein.

Strip Cap

Figure 3A:
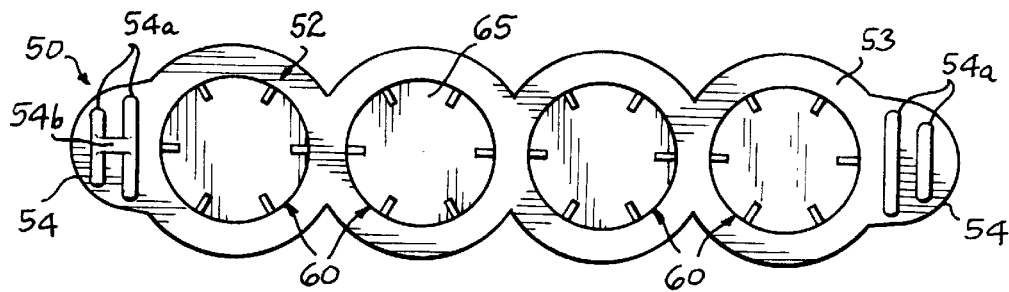
FIGS. 3A and 3B are respectively top plan and side elevational views of the strip cap shown in FIG. 1, with portions thereof cut away in FIG. 3B.
Figure 3B:
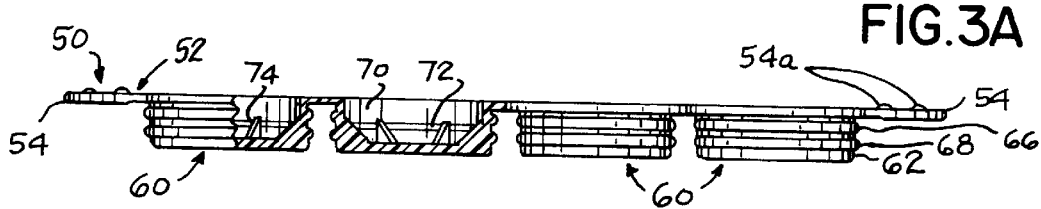

Strip cap 50 of multi-well slide assembly 20 is shown in greater detail in FIGS. 3A and 3B. In general, strip cap 50 includes a strip member 52 joining a plurality of cap members 60, one of which is provided for each well on multi-well slide 30.

Figure 4:
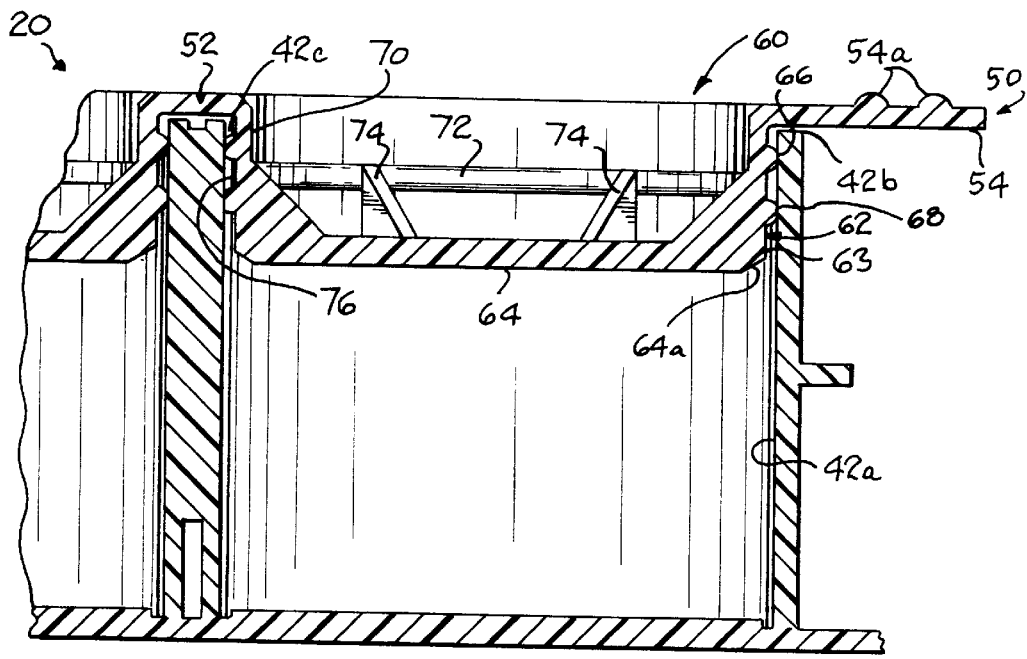
FIG. 4 is a cross-sectional view of one cap member in the strip cap of FIG. 2, illustrating the seal formed with a well on a multi-well slide assembly.

As best shown in FIG. 4, each cap member 60 includes an external wall 62 having a mating (or side wall) portion 63 and bottom portion 64. Mating portion 63 is typically cylindrical in shape, or other suitable shape to match the well with which it is being used. For example, while each well 40 in multi-well slide 30 is circular in cross-section, other cross-sectional profiles, such as square or rectangular, may also be utilized for each well, thereby necessitating an alternating shape for each cap member. Mating portion 63 of each cap member 60 may also be tapered, (e.g., at about 3°) to facilitate insertion of the cap member into the opening 42c of each well 42.

Bottom portion 64 of each cap member may be flat or domed. A flat profile provides a lower profile for the cap member, while a domed member may be useful in smaller designs to reinforce the cap member. An annular bevel at 64a is defined between mating portion 63 and bottom portion 64 to further facilitate insertion of each cap member into its associated well.

Returning to FIG. 4, one or more sealing rings, e.g. sealing rings 66, 68 are provided on each cap member to provide a compression seal against the inner wall 42a of each well 42 proximate the perimeter of opening 42c. Any number of sealing rings may be utilized, however, it has been found that one sealing ring may not provide as strong a seal as multiple sealing rings, in part due to the redundancy provided by multiple rings.

Moreover, it has been found that the use of multiple seals can provide a venting effect when the cap member is removed, which minimizes the vacuum created in the chamber, and consequently minimizes aerosol effects associated therewith.

Figure 5:
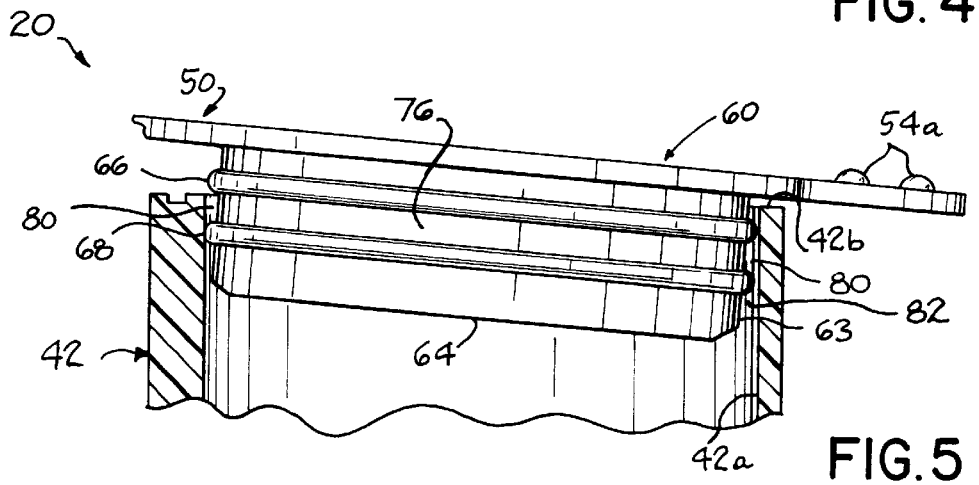
FIG. 5 is a side elevational view of one cap member in the strip cap of FIG. 2, with portions of a multi-well slide assembly cut away to illustrate removal of the strip cap from the multi-well slide assembly.

For example, as shown in FIG. 5, a channel 76 is defined between sealing ring 66, 68, such that as cap member 60 is removed from its associated well, channel 76 places well 42 in fluid communication with the atmosphere prior to complete removal of cap member 60. In particular, as cap member 60 is peeled off with a general tilting motion, channel 76 will first be exposed to the atmosphere as shown at 80. As the cap member is further peeled off and tilted, sealing ring 68 disengages from side wall 42a, as shown at 82, to place channel 76 in fluid communication also with the interior of well 42. The channel is therefore capable of venting air into the well as the cap member is removed to reduce the degree of vacuum, and therefore minimize any aerosol effects.

Figure 6:
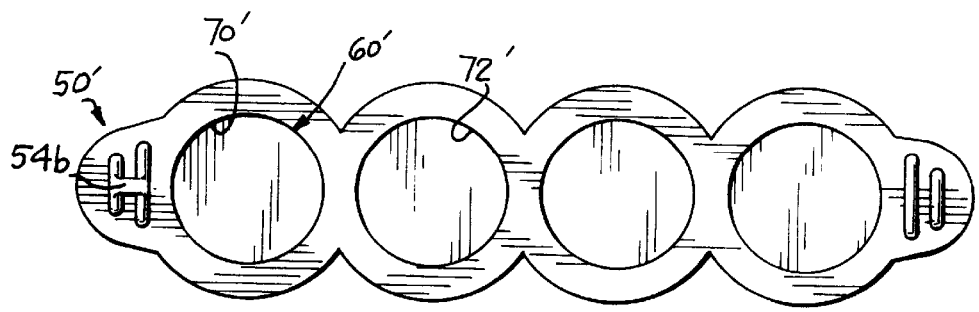
FIG. 6 is a top plan view of an alternate strip cap to that of FIG. 2.

Returning to FIG. 4, each cap member 60 also includes an internal wall 70 having an optional reinforcement ring 72 defined along the wall between sealing ring 66, 68 to assist and maintain the integrity of the wall. Moreover, a plurality of transversely-oriented ribs 74 may also be provided on the internal wall of each cap member to further add integrity to the cap member. Ribs 74 are not required, for example as shown by strip cap 50' of FIG. 6. Strip cap 50' includes plurality of cap members 60' that includes sealing rings as well as a reinforcement ring 72' on the internal wall 70'. However, no transverse ribs are provided on the internal wall thereof.

Strip member 52 (best shown in FIGS. 3B and 4) extends generally transverse to the mating portions of cap member 60 to form a flange 53 that overlaps the top edge 42b of each well 42 when the strip cap is secured to a multi-well slide. Flange 53 prevents contaminates such as dust or various biological agents from resting on the edge of each well. Moreover, the flange reduces well-to-well contamination. Furthermore, flange 53 prevents the cap member from being inserted too far into the well, and keeps the user's finger off the top edge of the well to further minimize contamination thereof.

A pair of tabs 54 also extend from the ends of strip member 52. Each includes fingernail ridges 54a that assist in the manual removal of the strip cap. Moreover, one of the tabs 54 may also include an orientation marking 54b extending transverse to ridges 54a so that strip member 52 may be secured to a multi-well slide in a repeatable, predetermined orientation. Consequently, the risk of cross-contamination due to placing strip member 52 on backwards relative to a previous installation of the same is reduced.

The design of strip member 52 also permits tweezers to be utilized to remove the strip cap by grasping flange 53. Moreover, if strip cap 50 is constructed of a soft material, a knife or scalpel may be used to separate the individual cap members such that each is separately removable with tweezers. This enables wells to be opened and closed individually. For example, this may enable a sealed control sample to be maintained while various testing operations are performed on the test samples. It also enables various samples to be inoculated at different starting times to account for the different growth rates of various cell lines.

Typically, strip cap 50 is integrally injection molded with a flexible material such as a USP Class 6 or compatible medical-rated plastic that is not toxic to test samples or other biological agents that may come in contact with the strip cap during testing. For example, one suitable material is low-density polyethylene, although other materials, such as high density polyethylene or polypropylene, among others, may also be used.

The design of strip cap 50 provides significant advantages over conventional designs. For example, strip cap 50 provides a strong seal that is suitable for centrifugation as well as transportation of multi-well slide assemblies. The seal provided by such a strip cap enables cell cultures of living cell lines to be commercially prepared in wells, sealed within the assemblies along with a suitable transport medium, and then sold, stored and/or transported to customer laboratories for later use. Customers are then able to merely remove the strip caps and inoculate the cell lines as desired to perform testing, without first having to culture their own cell lines.

Another significant advantage is that the strip caps are replaceable such that after inoculation, the multi-well slide assemblies may be resealed and utilized during centrifugation. This seal may assist in maintaining the media's pH during shipment as well as during the diagnostic process.

Frame

Figure 7:
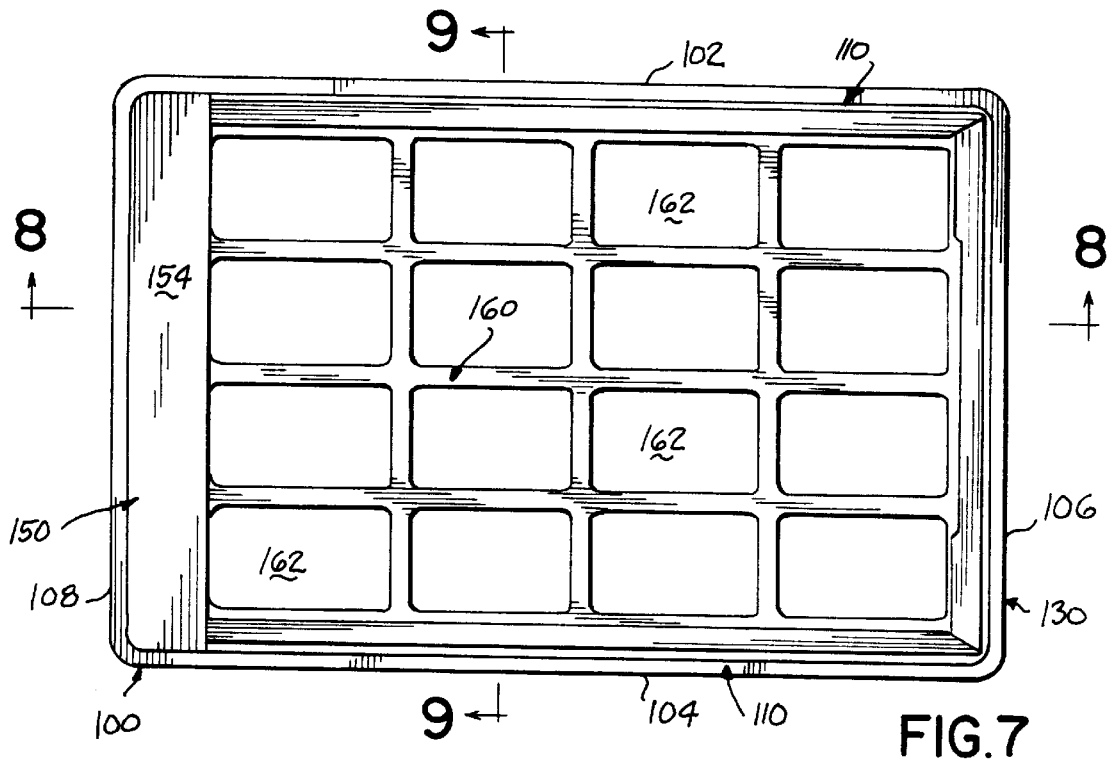
FIG. 7 is a top plan view of the frame shown in FIG. 1.

FIG. 7 illustrates frame 100 of FIG. 1 in greater detail. The frame includes left and rights sides 102 and 104 and front and rear ends 106 and 108. A pair of opposing channels 110 are provided along sides 102, 104 and a pair of retaining mechanisms 130, 150 are disposed at the ends 106,108 thereof. A lower support member 160 with a plurality of access apertures 162 defined therein supports and separates the opposing channels at a predetermined distance from one another.

Frame 100 is typically sized at about 5.025" by 3.365" to provide a footprint that is substantially similar to a conventional microwell plate or multi-well cell culture dishes (e.g., 6, 12, 24, 48, 96, 384, etc. well plates). Moreover, the height of frame 100 is slightly smaller than that of a microwell plate. The dimension, enable frame 100 to be used with the various processing and analysis equipment that currently exist for processing microwell plates or multi-well cell culture dishes. For example, various liquid handling systems such as washers, dispensers, robotic fingers, pipettors, and other ancillary equipment such as centrifuges having centrifuge buckets/carriers have been developed to utilize assemblies having such footprint. Moreover, various optical viewers, including microscopes (specifically, the stages thereof), spectrophotometers, luminometers, fluorimeters, and colorimetric readers, among others, may also be compatible with such a footprint. Other robotics, manufacturing systems and coating systems, may also recognize such footprint.

Frame 100 is typically constructed of an autoclavable, chemically resistant, strong, and freezable material such as Noryl plastic available from General Electric, which is a 20% glass-filled modified polyphenylene oxide. Other materials, including various plastics and metals, whether transparent or opaque, may also be used consistent with the invention. The frame may or may not be reusable.

Figure 8:
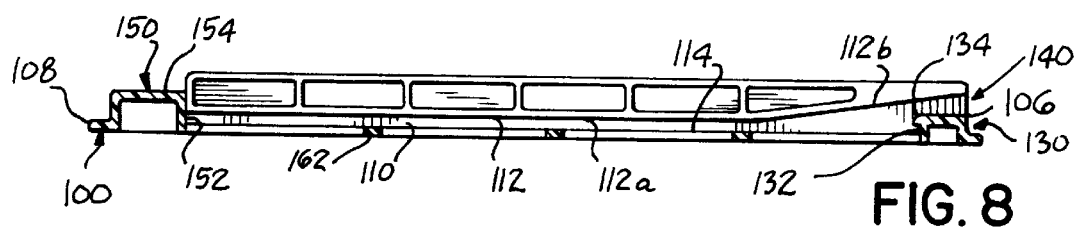
FIG. 8 is a side cross-sectional view of the frame, taken through lines 8—8 of FIG. 7.
Figure 9:
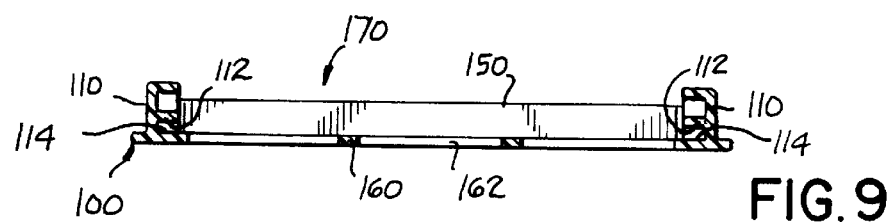
FIG. 9 is an end cross-sectional view of the frame, taken through lines 9—9 of FIG. 7.

As shown in FIGS. 8 and 9, each opposing channel 110 of frame 100 includes upper and lower walls 112, 114. Upper wall 112 is partitioned into a retaining portion 112a that extends along a longitudinal axis of the channel and parallel with lower wall 114. An access portion 112b of upper wall 112 extends at an acute angle relative to the longitudinal axis, terminating at an open end to define access opening 140 through which multi-well slide assemblies are inserted and removed from frame 100. It should be appreciated that each channel may be defined by other structure in frame 100. For example, lower wall 114 may be defined on a separate member, rather than being contiguous with lower support member 160. In addition, should the opposing ends of the particular reaction vessel assemblies to be retained by frame 100 not be planar (as with multi-well slide assemblies 30), alternate configurations and dimensions of the channels may be utilized to retain suitable structure on the reaction vessel assemblies for use therewith.

Retaining mechanism 130 includes a stop member 132 and retaining mechanism 150 includes a stop member 152, each of which close off an end of both opposing channels. Moreover, retaining mechanism 130 includes a detent 134 that extends from stop member 132 towards the opposite end of the channel. The detent 134 is spaced from lower wall 114 approximately the same distance as the upper wall retaining portion 112a—approximately the width of the structure that is retained within the channels. Detent 134 is beveled along an upper surface thereof to facilitate movement of retained objects over the detent. Retaining mechanism 150 may also include an upper surface 154 (See FIG. 7), which may include integrally-molded alphanumeric information, or which may provide a writeable surface or space for a label such that an operator can identify or annotate the assembly.

It should be appreciated that various other retaining mechanisms may also be used to close the ends of the opposing channels and thereby secure reaction vessel assemblies within the frame. For example, either or both of the retaining mechanisms may be removable to selectively open or close the end of the opposing channels. The removal or retaining mechanisms may be secured by any number of means, including clips, screws, detents, tabs, etc. In general, any structure that abuts retained objects to prevent movement thereof beyond the ends of the channels may be used. Moreover, the retaining mechanisms may abut such objects either within the channels or in the space defined therebetween. However, it is believed that the illustrated structure provides advantages over various alternatives as no moving parts are required, and as the configuration thereof is relatively simple and reliable for manufacturing and use.

Frame 100 is configured to hold four multi-well slides such as multi-well slide assemblies 20 of FIG. 1. However, frame 100 could be used to secure other reaction vessel assemblies, including various planar assemblies such as slides, plates, wafers, etc., whereby the planar surfaces retained within by the channels are coplanar with surrounding structure on the assembly. Various other assemblies, including microarrayed surfaces, microwell and multi-well plates, flasks, etc., may also be used. Moreover, the retained surfaces need not be co-planar with the surrounding structure of the assembly nor need they have a planar shape. In general, any reaction vessel assemblies having opposing ends suitable for retention within a pair of channels may be secured in the manner disclosed herein in frame 100.

Figure 10A:
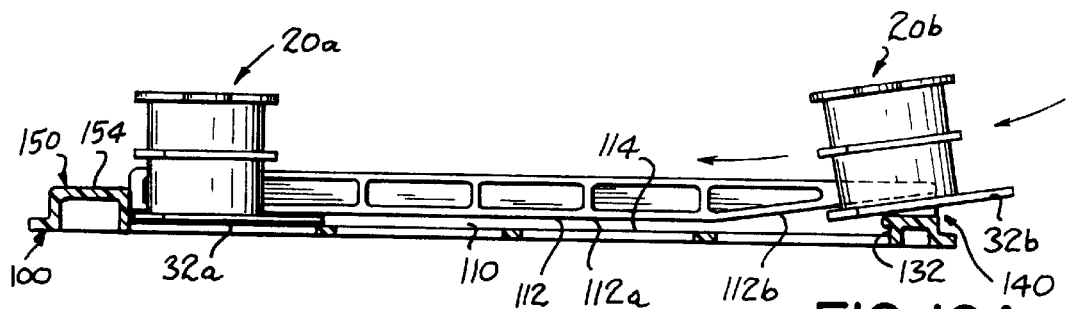
FIGS. 10A–10C are side cross-sectional views of the frame of FIG. 6, illustrating insertion of a plurality of multi-well slides into the frame.
Figure 10B:
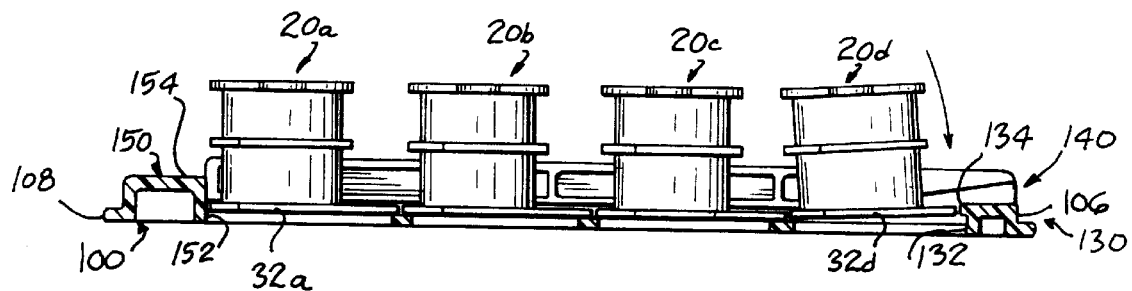
Figure 10C:
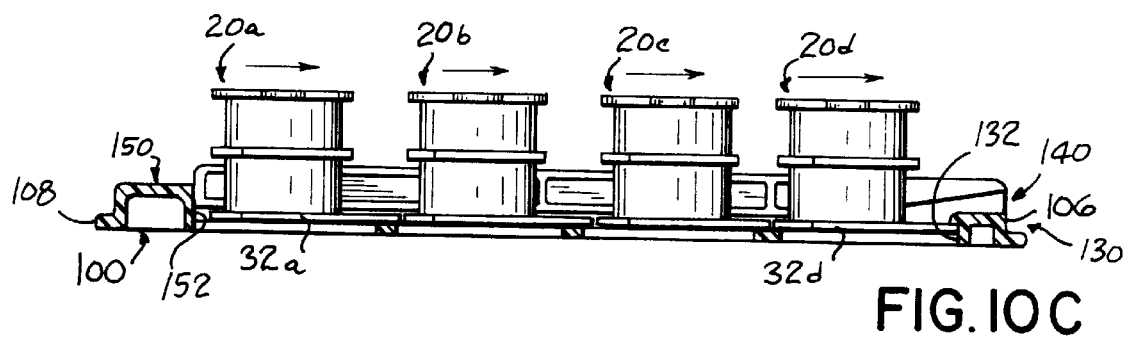

FIGS. 10A–10C illustrate the insertion of multi-well slide assemblies into frame 100. First, FIG. 10A illustrates the insertion of a second multi-well slide assembly 20b through access opening 140 of frame 100, with a first multi-well slide assembly 20a already retained therein. It should be noted that assembly 20b is slightly angled to orient plate 32b thereof between the upper and lower walls 112, 114 of frame 100. To insert assembly 20b into frame 100, the assembly is slid toward the rear end of the frame, in the general direction toward retaining mechanism 150.

Next, as illustrated in FIG. 10B, the insertion of three assemblies 20a–20c into frame 100 proceeds in much the manner described above. To insert a fourth assembly 20d, however, each of the first three assemblies 20a–20c must be slid rearward to abut one another as well as abut stop member 152 of retaining mechanism 150. This provides enough separation within each channel 110 to permit assembly 20d to be slid into frame 100 a sufficient distance to be tilted downward past detent 134. The spacing provided between detent 134 and stop member 152 is equal to or slightly larger than the combined widths of the four assemblies. In the alternative, the distance between detent 134 and stop member 152 may be slightly less than the total width of assemblies 20a–20d such that some resistance is encountered when inserting or removing assembly 20d from frame 100.

Next, as illustrated in FIG. 10C, once all assemblies 20a–20d are disposed between channels 110, all assemblies are slid forward toward retaining mechanism 130 to abut assembly 20b against stop member 132, and thereby leave a small gap between assembly 20a and stop member 152. Consequently, assemblies 20a–20d are secured within the channels.

The gap remaining within each channel once all assemblies 20a–20d are inserted therein may be slightly larger than the width of detent 134 to permit each assembly to be removed easily when slid rearward, yet retained securely when the assemblies are slid forward. In the alternative, the gap may be made slightly less than the width of the detent, such that some resistance must be overcome to dislodge an assembly when all are retained within the frame.

Figure 11:
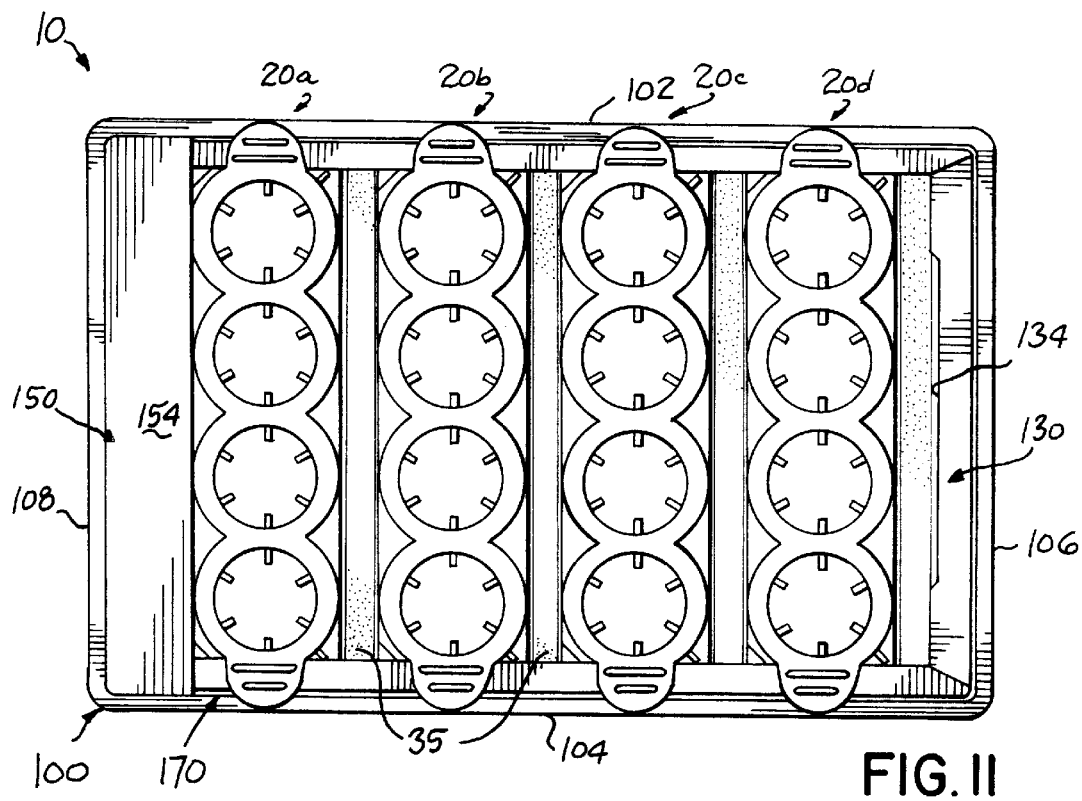
FIG. 11 is a top plan view of the multi-slide assembly of FIG. 1.
Figure 12:
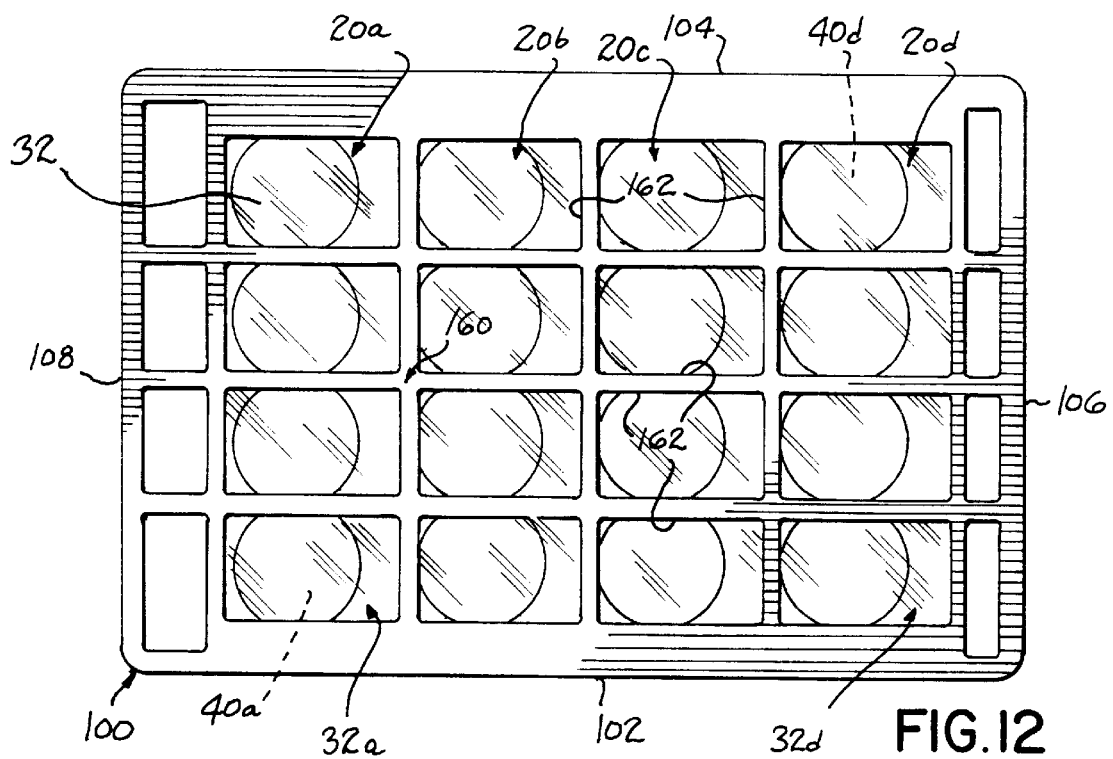
FIG. 12 is a bottom plan view of the multi-slide assembly of FIG. 1.

As shown in FIGS. 11 and 12, frame 100 provides clear access to both the top and bottom portions of each multi-well slide assembly 20. As shown in FIG. 11, as well as FIG. 8, a single upper access aperture 170 is typically defined in frame 100 such that free access to each of assemblies 20a–20d is provided. Moreover, as shown in FIG. 12, lower support member 160 includes one or more access apertures 162 that permit assemblies 20a–20d to be viewed and accessed through the bottom of the frame (See, e.g., wells 40a, 40d, which are visible through clear plates 32a, 32d). As shown in FIG. 12, access apertures 162 may be defined by voids formed in member 160. In the alternative, apertures 162 may be formed by transparent portions of member 160. Moreover, member 160 may be simply constructed of a single planar member formed with transparent material. In these latter instances, the access apertures would merely provide visual access apertures that permitted viewing but not physical access.

Access aperture 162 enable viewing of cell cultures from the top or bottom of the assembly, e.g. by using an optical viewer such as a microscope. Moreover, by configuring access apertures 162 as voids, an optical viewer may be oriented directly proximate the slide plates of assemblies 20a–20d if necessary.

In the alternative, access apertures may be omitted from frame 100, e.g., by providing a planar opaque lower support member. Such a design may be useful, for example, to provide high contrast with the cell cultures for use with other types of optical viewers.

An additional function of member 160 is to provide support for assemblies 20a–20d, particularly during centrifugation. When utilizing multi-well slide assemblies 30 having removable upper structures, bowing might otherwise break the well seals and cause leakage and contamination of the cell cultures during this process. The design of lower support member 160 therefore supports assemblies 30 to prevent any such bowing.

Figure 13:
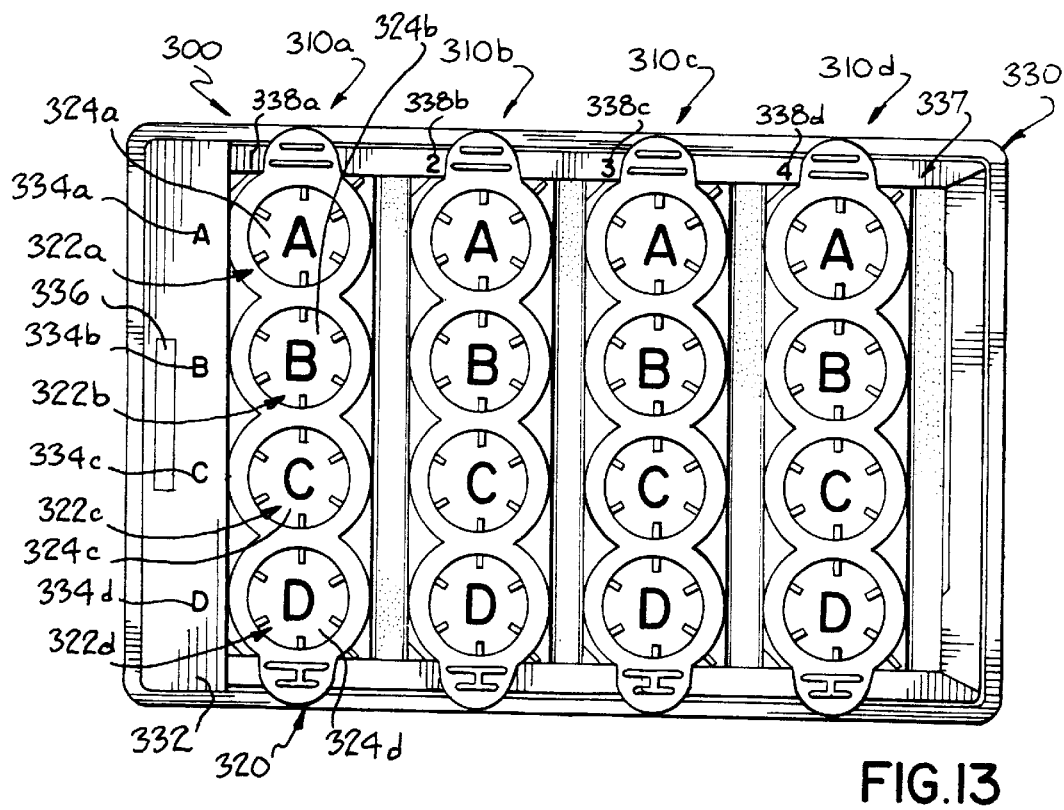
FIG. 13 is a top plan view of an alternate multi-slide assembly consistent with the invention.

FIG. 13 illustrates another multi-slide assembly 300 that illustrates the use of coordinating indicia on a plurality of multi-well slide assemblies 310a–310d and a frame 330. For example, each multi-well slide assembly, e.g., multi-well slide assembly 310a, may include a strip cap 320 in which each cap member 322a–322d includes an indicia 324a–324d that assists in identifying a particular well. Typically, each indicia 324a–324d is one of a series of letters or numbers (e.g., letters A–D as shown in FIG. 13) that are matched with corresponding indicia identifying each well on the associated multi-well slide (not shown in FIG. 13), so that the strip cap may be removed and replaced in a repeatable orientation. Each indicia may be integrally molded into the bottom portion of each cap member, or in the alternative, may be printed onto the surface of each cap member in any suitable manner known in the art.

Moreover, the indicia on each cap member may also coordinate with matching indicia 334a–334d molded or printed onto surface 332 of frame 330 to provide a visual cue that facilitates proper installation of each multi-well slide assembly 310a–310d into frame 330. Frame 330 may also have additional indicia, e.g., a manufacturer's logo 336, as well as transverse indicia 338a–338d located on surface 337. Indicia 338a–338d typically includes a series of letters or numbers (e.g., numbers 1–4 as shown in FIG. 13) to identify each multi-well slide assembly 310a–310d when installed in frame 330. Indicia 338a–338d typically are located so that they are visible when assemblies 310a–310d are installed in the frame. Moreover, indicia 334a–334d and 338a–338d cooperate to identify each well in assembly 300 (e.g., the well in the top left corner is identified as well A1, and the well in the bottom right corner is identified as well D4). Other indicia and manners of identifying wells and the like may also be used in the alternative.

Method of Use

Multi-slide assembly 10 and its various components have numerous uses in the biomedical diagnostics applications. For example, as described in greater detail below, one principle use for multi-slide assemblies consistent with the invention is in diagnosing the presence of a virus in a test sample such as a patient specimen. However, it should be appreciated that this usage is but one of numerous other applications where it is desirable to perform life science cell and tissue culturing, such as in research and diagnostic screening, viral screening, cancer screening, drug screening, etc. Therefore, the invention should not be limited to the particular application described herein.

For viral diagnostic screening, a live cell line is grown in each multi-well slide assembly. The cell lines selected typically have a particular sensitivity to a given virus for which is desired to determine the presence/non-presence thereof in a test sample. The virus uses the cell to replicate itself resulting in cytopathic effect (CPE) or an antigen that can be detected using a monoclonal antibody.

For example, for the influenza and parainfluenza viruses, the chosen cell line may be RHMK (Rhesus Monkey Kidney) cells. For CMV (cytomegalovirus), the chosen cell line may be MRC-5 (Human Lung). For VZV (Varicella-Zoster Virus), the cell line may be A549. For adenovirus, the cell line may be A549, or alternatively, HEp-2 (Human Larynx). For other viruses such as enterovirus, RSV (Respiratory Syncytial Virus), HSV (Herpes Simplex Virus), and others, the cell line may be any of the RHMK, MRC-5, A549, or HEp-2. Live cell lines or cultures, which are sensitive to other viruses, may also be used in the alternative.

Cells may be grown in each multi-well slide assembly in a clinical laboratory in a manner known in the art. In the alternative, the assemblies may be prepared by a manufacturer of such assemblies using commercially-grown cells.

In either case, the empty wells within each assembly are inoculated with cells and the cells are cultured in a growth medium such as Dulbecco's Modified Eagle's Medium (DMEM). When the cells are grown in the clinical laboratory in which the diagnostic testing is to be performed, the growth medium may be removed such that test samples may be used to inoculate the cell culture. If, however, the assemblies are prepared by a manufacturer, the growth medium may be removed and replaced with a transport medium that keeps the cells stable during transport. The multi-well slide assemblies are then sealed with strip caps, packaged and transported to customers. Moreover, such assemblies may be mounted in groups of four within frames for packaging and transport.

It should be appreciated that, given the flexibility provided by the multi-well slide assemblies as well as the use of multiple assemblies in a frame, any number of combinations of cell types may be provided in each multi-slide assembly. Typically, each well in a multi-well slide assembly has the same cell type, since otherwise different culturing times for different cell types may make it more difficult to ensure adequate growth of cell cultures within a given assembly.

Once cell cultures are formed in the multi-well slide assemblies, selected assemblies are inoculated with test samples such as patients' specimens. Multi-well slide assemblies may be inoculated individually, or alternatively, can be placed in a frame with any desired combination of cell cultures represented in the different assemblies.

If the multi-well assemblies are pre-manufactured assemblies supplied with commercially-grown cell cultures, the strip caps are first removed. Next, the transport medium may be aspirated from the wells, and the wells are optionally rinsed, e.g., with a rinse agent such as Hanks Balanced Salt Solution (HBSS). In addition, a small amount (e.g. about 0.02 ml) of growth/maintenance medium such as EMEM (Eagle's Minimum Essential Medium) or serum free medium, is optionally added to maintain the cell cultures during inoculation and to buffer test sample toxicity. Typically, the amount of growth/maintenance medium is small so that any viruses in the test sample are maintained in close proximity to the cell culture.

Next, predetermined amounts of test samples are introduced into the wells to inoculate the cell cultures. Then, the strip caps are reinstalled on each of the assemblies in preparation for centrifugation.

If the multi-well slide assemblies are not yet disposed in a frame, they may be so mounted such that the frame may be placed in a suitable microwell plate carrier bucket of a centrifuge. Centrifugation is then performed on all the assemblies concurrently, e.g. at 700 G's for about one hour. Centrifugation assists in introducing any viruses into a cell culture more rapidly to speed up the diagnostic process.

Next, once the cell cultures have been centrifuged, the strip caps are removed from the assemblies and a growth medium is optionally added. The assemblies are then covered with lids and are incubated at an elevated temperature for a predetermined time (e.g., 360 Celsius for multiple days in a $CO_2$ incubator). The lids are utilized in lieu of the strip caps in this process to permit some degree of $CO_2$ transfer during incubation. In some applications, strip caps may instead be utilized to seal the wells from air. During incubation, it may also be desirable to periodically replace the growth medium as necessary.

Upon completion of incubation, the test samples may be analyzed for potential cytopathic effects or antigen expression. Typically, the lids or strip caps are removed and any growth media is aspirated from the cell cultures. The cell cultures may be fixed, stained, etc., as necessary to permit suitable analysis of the cell cultures. For example, the cells may be fixed with acetone, dried and then stained with a drop of appropriate monoclonal conjugate. The slide containing the cells is incubated, rinsed with PBS and observed under a microscope.

Figure 14:
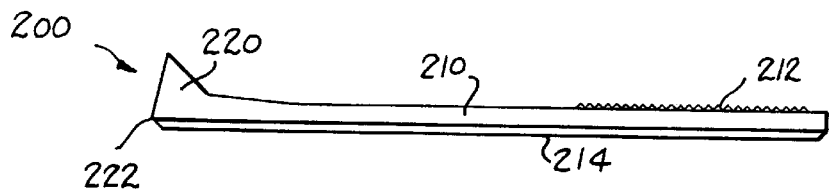
FIG. 14 is a side elevational view of the opener shown in FIG. 1.
Figure 15:
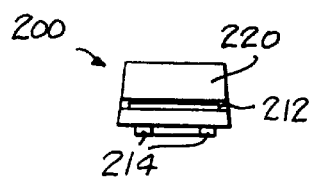
FIG. 15 is an end elevational view of the opener shown in FIG. 1.

Next, it may be desirable to remove the upper structure of the multi-slide assemblies from the slide plate, typically by inserting a suitable opener to pry the upper structure from the plate. For example, one suitable pry-bar opener is illustrated at 200 at FIG. 1. This opener is illustrated in more detail in FIGS. 14–15. Opener 200 generally includes an elongated member 210 having grip ridges 212 and strengthening ribs 214 disposed on opposing surfaces thereof. A pry member 220, which extends at roughly a 90° angle relative to the elongated member, is levered at point 222 to form a fulcrum from which a separation force may be applied to a multi-well slide assembly. Member 220 typically engages between the upper structure and slide plate of a multi-well slide assembly when the elongated member extends roughly perpendicular to the plane of the slide plate, with the fulcrum defined on the pry member engaging along the frosted writing surface of the slide plate.

By virtue of its angled orientation, the opener is able to fit between the various assemblies in the frame to perform the separation. Moreover, when the upper structure of an adjacent assembly in the frame has already been removed, the angled orientation of the opener prevents damage or contamination to the cells on the adjacent slide plate when removing the upper structure of an assembly.

Alternatively, the cells may be fixed and processed once the upper structures have been removed from the slide plates from each assembly. Finally, cover slips may then be applied over the fixed and processed cells, whereby the cells are then ready for visual microscopic analysis.

Cell cultures may be analyzed by various optical viewing devices; including microscopes, spectrophotometers, luminometers, etc. Moreover, by virtue of the open access to both surfaces of the slide plates through frame 100, analysis may be performed from either side of the slide plates. Moreover, the assemblies may be removed from the frame and separately analyzed if desired.

Therefore, it should be appreciated that the various embodiments of the invention provide significant advantages in simplifying and accelerating diagnostic testing. Moreover, it has been found that the various embodiments also provide improved performance over conventional cell culture vessels such as dram vials and culture tubes as they have been found to be more sensitive, often experiencing more pronounced cytopathic effects more quickly. Moreover, it has been found that cross-contamination is reduced compared to various multi-vessel assemblies such as multi-well plates. Another advantage is that the need for glass cover slips, as is often required for cell growth and testing with dram vials or Petri dishes, is eliminated. Moreover, the inherent hazards associated with the use of glass in a laboratory are avoided. Other advantages of the various embodiments of the invention will be apparent to one skilled in the art.

Various modifications may be made to the various embodiments without departing from the spirit and scope of the invention. Therefore, the invention lies in the claims hereinafter appended.

We claim:

1. A strip cap for use in sealing an opening in at least one reaction vessel having an internal wall defining the opening, the strip cap including:
   (a) a cap member having an external wall, a mating portion of which is configured to abut the internal wall of the reaction vessel around a perimeter of the opening; and
   (b) a sealing ring circumscribing the external wall of the cap member, the sealing ring configured to form a compression seal with the internal wall of the reaction vessel.

2. The strip cap of claim 1, further comprising a second sealing ring circumscribing the external wall of the cap member in spaced apart relationship with the first sealing ring, the first and second sealing rings defining a vent channel therebetween, the vent channel placing the reaction vessel in fluid communication with the atmosphere when the strip cap is partially tilted from the reaction vessel.

3. The strip cap of claim 2, further comprising a reinforcement ring circumscribing an internal wall of the cap member intermediate the first and second sealing rings.

4. The strip cap of claim 1, further comprising a plurality of ribs, each extending between bottom and side portions of the internal wall of the cap member.

5. The strip cap of claim 1, wherein the mating portion of the external wall is cylindrical.

6. The strip cap of claim 5, wherein the mating portion of the external wall is tapered.

7. The strip cap of claim 6, wherein the external wall further comprises a bottom portion extending generally perpendicular to the mating portion thereof, and an annular bevel joining the mating and bottom portions of the external wall.

8. The strip cap of claim 1, further comprising a plurality of cap members disposed in a linear arrangement and joined by a strip member, and each including a sealing ring configured to mate with one of a linear arrangement of reaction vessels.

9. The strip cap of claim 8, wherein the strip member includes a flange portion circumscribing each cap member and configured to overlap an end portion of the internal wall of each cell culture member proximate the opening thereof.

10. The strip cap of claim 8, wherein the plurality of reaction vessels comprise a multi-well slide including a plurality of wells coupled to a slide plate, wherein each reaction vessel includes one of the plurality of wells.

11. The strip cap of claim 8, wherein the plurality of cap members, the plurality of sealing rings, and the strip member are molded as an integral unit.

12. The strip cap of claim 11, wherein the plurality of cap members, the plurality of sealing rings, and the strip member are formed from a flexible material.

13. The strip cap of claim 12, wherein the plurality of cap members, the plurality of sealing rings, and the strip member are formed of a material selected from the group consisting of low density polyethylene, high density polyethylene, polypropylene, and a thermoplastic elastomer.

14. A multi-well slide assembly, comprising:

(a) a slide plate;

(b) a plurality of wells coupled to the slide plate, each well including an internal wall defining an opening to the well; and (c) a strip cap, including:

(1) a strip member;

(2) a plurality of cap members coupled to the strip member, each cap member having an external wall, a mating portion of which is configured to abut the internal wall of one of the plurality of wells around a perimeter of the opening thereto; and (3) a plurality of sealing rings, each sealing ring circumscribing the external wall of one of the plurality of cap members, and each sealing ring configured to form a compression seal with the internal wall of one of the plurality of wells.

15. The multi-well slide assembly of claim 14, further comprising a second plurality of sealing rings, each circumscribing the external wall of one of the plurality of cap members in spaced apart relationship with the first sealing ring thereon, wherein the first and second sealing rings on each cap member define a vent channel therebetween, the vent channel placing the well in which the cap member is disposed in fluid communication with the atmosphere when the cap member is partially tilted from the well.

16. The multi-well slide assembly of claim 14, further comprising a biological or chemical substance housed within each of the plurality of wells, the biological or chemical substance selected from the group consisting of a cell culture, a biochemical reagent, a biological substance, and combinations thereof.

17. The multi-well slide assembly of claim 16, further comprising a transport medium housed within each of the plurality of wells.

18. A frame for use in retaining a plurality of reaction vessels, each reaction vessel of the type including opposing ends, the frame comprising;

(a) a pair of opposing channels facing in different directions from one another, the pair of opposing channels including first and second ends and configured to slidably receive the opposing ends of each reaction vessel; and (b) first and second retaining mechanisms respectively disposed proximate the first and second ends of the pair of opposing channels and configured to retain each reaction vessel within the pair of opposing channels.

19. The frame of claim 18, wherein each reaction vessel includes opposing engagement members defining the opposing ends such that the pair of opposing channels engage the engagement members of each reaction vessel.

20. The frame of claim 18, wherein each reaction vessel includes a plate on which is defined the opposing ends such that the pair of opposing channels engage the plate of each reaction vessel.

21. The frame of claim 20, wherein the first retaining mechanism includes a first stop member restricting movement of the reaction vessels beyond the first end of the pair of opposing channels.

22. The frame of claim 21, further comprising an access opening defined proximate the first end of the pair of opposing channels.

23. The frame of claim 22, wherein each channel has a longitudinal axis and includes opposing upper and lower walls respectively configured to restrict movement of the plate of each reaction vessel in a direction perpendicular to a surface of the walls, the upper wall of each channel including a retaining portion and an access portion, the access portion at least partially defining the access opening, and the access portion of the upper wall of each channel extending toward the first end of the channel from a point intermediate the first and second ends of the channel, and extending away from the lower wall of the channel at an acute angle relative to the longitudinal axis of the channel.

24. The frame of claim 22, wherein the first retaining mechanism further includes a detent extending from the first stop member toward the second end of each channel.

25. The frame of claim 24, wherein the detent is spaced from the lower wall of each channel at substantially the same distance as the retaining portion of the upper wall of the channel.

26. The frame of claim 25, wherein the plate of each reaction vessel has a thickness, and wherein the detent and the retaining portion of the upper wall of each channel are spaced from the lower wall at distance substantially equal to the thickness of the plate of each reaction vessel.

27. The frame of claim 25, wherein each reaction vessel has a width defined along the longitudinal axis of each channel when the reaction vessel is slidably received between the pair of opposing channels, and wherein the detent includes an end spaced from the second end of the channel at a distance that is substantially the same as a sum of the widths of the plurality of reaction vessels.

28. The frame of claim 20, wherein the frame includes a lower support member coupled to and extending between the pair of opposing channels, the lower support member configured to support each reaction vessel in a direction generally perpendicular to the plate thereof.

29. The frame of claim 28, wherein the frame defines an upper access aperture extending between the pair of opposing channels and between the first and second retaining mechanisms.

30. The frame of claim 28, wherein the lower support member defines at least one access aperture through which is visible at least one of the plurality of reaction vessels.

31. The frame of claim 30, wherein the access aperture is defined by a void in the lower support member.

32. The frame of claim 30, wherein the lower support member includes a transparent material forming a visual access aperture.

33. The frame of claim 18, wherein the second retaining mechanism includes a stop member restricting movement of the reaction vessels beyond the second end of the pair of opposing channels.

34. The frame of claim 18, wherein each reaction vessel includes a multi-well slide including a plurality of wells.

35. The frame of claim 34, wherein the frame is configured to retain four multi-well slides, each including four wells on each slide.

36. The frame of claim 18, wherein the frame has a footprint that is substantially similar to that of a microwell plate, and has a height that is no greater than that of a microwell plate.

37. The frame of claim 18, wherein each reaction vessel is selected from the group consisting of a cell culture vessel, a multi-well slide, a flask, a dish, a culture tube, a wafer, a slide, a plate, a disc and a microarrayed surface.

38. The frame of claim 18, wherein the pair of opposing channels face one another.

39. An assembly, comprising:

(a) a plurality of reaction vessels, each including opposing ends; and (b) a frame retaining the plurality of reaction vessels, the frame including:

(1) a pair of opposing channels including first and second ends and configured to slidably receive the opposing ends of the plurality of reaction vessels; and (2) first and second retaining mechanisms respectively disposed proximate the first and second ends of the pair of opposing channels and configured to retain each reaction vessel within the pair of opposing channels.

40. The assembly of claim 39, wherein each reaction vessel includes a multi-well slide including a plurality of wells defined on a slide plate, and wherein the opposing ends of each multi-well slide are defined on the slide plate such that the pair of opposing channels engage the slide plate of each multi-well slide.

41. The assembly of claim 40, wherein:

(a) the first retaining mechanism includes a first stop member restricting movement of the multi-well slides beyond the first end of the pair of opposing channels;

(b) the second retaining mechanism includes a stop member restricting movement of the multi-well slides beyond the second end of the pair of opposing channels;

(c) each channel has a longitudinal axis and includes opposing upper and lower walls respectively configured to restrict movement of the slide plate of each multi-well slide in a direction perpendicular to a surface of the walls, the upper wall of each channel including a retaining portion and an access portion, the access portion at least partially defining an access opening for the frame, and the access portion of the upper wall of each channel extending toward the first end of the channel from a point intermediate the first and second ends of the channel, and extending away from the lower wall of the channel at an acute angle relative to the longitudinal axis of the channel; and (d) the first retaining mechanism further includes a detent extending from the first stop member toward the second end of each channel, the detent spaced from the lower wall of each channel at substantially the same distance as the retaining portion of the upper wall of the channel.

42. The assembly of claim 41, wherein:

(a) the slide plate of each multi-well slide has a width and a thickness;

(b) the detent and the retaining portion of the upper wall of each channel are spaced from the lower wall at distance substantially equal to the thickness of the slide plate of each multi-well slide; and (c) the detent includes an end spaced from the second end of the channel at a distance that is substantially the same as a sum of the widths of the slide plates of the plurality of multi-well slides.

43. The assembly of claim 40, wherein the frame includes a lower support member coupled to and extending between the pair of opposing channels, the lower support member configured to support each multi-well slide in a direction generally perpendicular to the slide plate thereof, the lower support member defining at least one access aperture through which is visible a test sample disposed in one of the plurality of wells on one of the plurality of multi-well slides.

44. The assembly of claim 40, wherein the plurality of wells on each multi-well slide are removably coupled to the respective slide plates via ultrasonic welds.

45. The assembly of claim 40, wherein each well on the plurality of multi-well slides includes an internal wall defining an opening to the well, the assembly further comprising a strip cap coupled to at least one of the multi-well slides, the strip cap including:

(a) a strip member;

(b) a plurality of cap members coupled to the strip member, each cap member having an external wall, a mating portion of which is configured to abut the internal wall of one of the plurality of wells around a perimeter of the opening thereto; and (c) a plurality of sealing rings, each sealing ring circumscribing the external wall of one of the plurality of cap members, and each sealing ring configured to form a compression seal with the internal wall of one of the plurality of wells.

46. The assembly of claim 39, wherein the pair of opposing channels face one another.

47. A reaction vessel, comprising:

(a) a slide plate;

(b) a sidewall member including a sidewall including an end and having a thickness, and an energy director including a base coupled to an end of the sidewall and having a width; and (c) an ultrasonically-welded and controllably-weakened bond removably securing the sidewall member to the slide plate, the bond comprising a fused junction between the slide plate and the sidewall member and formed of substantially the entire energy director, wherein the slide plate and sidewall member form a mating surface having a width between the width of the energy director and the thickness of the sidewall.

48. The reaction vessel of claim 47, wherein the sidewall member comprises an upper structure defining in cooperation with the slide plate a plurality of wells.

49. The reaction vessel of claim 47, wherein the slide plate and the sidewall member are formed of chemically-resistant plastic.

* * * * *